United States Patent
Deng et al.

(10) Patent No.: US 10,829,510 B2
(45) Date of Patent: Nov. 10, 2020

(54) METHOD FOR PREPARING SUCRALOSE-6-ACETATE IN BIPHASIC LIQUID-LIQUID SYSTEM

(71) Applicant: ZHEJIANG NHU COMPANY LTD., Shaoxing (CN)

(72) Inventors: Fuxiang Deng, Shaoxing (CN); Yu Ding, Shaoxing (CN); Wei Xue, Shaoxing (CN); Sheng Yu, Shaoxing (CN); Wenwu Yan, Shaoxing (CN); Ming Yu, Shaoxing (CN); Yougui Zhou, Shaoxing (CN); Haoran Li, Shaoxing (CN)

(73) Assignee: ZHEJIANG NHU COMPANY LTD., Shaoxing (CN)

(*) Notice: Subject to any disclaimer, the term of this patent is extended or adjusted under 35 U.S.C. 154(b) by 8 days.

(21) Appl. No.: 16/300,426

(22) PCT Filed: May 18, 2017

(86) PCT No.: PCT/CN2017/084877
§ 371 (c)(1),
(2) Date: Nov. 9, 2018

(87) PCT Pub. No.: WO2018/086330
PCT Pub. Date: May 17, 2018

(65) Prior Publication Data
US 2019/0092801 A1  Mar. 28, 2019

(30) Foreign Application Priority Data

Nov. 11, 2016  (CN) .......................... 2016 1 1038346

(51) Int. Cl.
*C07H 13/04*  (2006.01)
*C07H 1/00*  (2006.01)
(52) U.S. Cl.
CPC ............... *C07H 13/04* (2013.01); *C07H 1/00* (2013.01)

(58) Field of Classification Search
None
See application file for complete search history.

(56) References Cited

U.S. PATENT DOCUMENTS

| 3,871,964 A | * | 3/1975 | Huper | ........................ | C08F 8/00 |
| | | | | | 435/44 |
| 2018/0162892 A1 | * | 6/2018 | Eilers | ........................ | C07H 1/00 |

FOREIGN PATENT DOCUMENTS

| CN | 102070678 | 5/2011 |
| CN | 102167712 | 8/2011 |
| CN | 105131050 | 12/2015 |

* cited by examiner

*Primary Examiner* — Dale R Miller
(74) *Attorney, Agent, or Firm* — Jiwen Chen; Jacobson Holman PLLC

(57) ABSTRACT

The present invention discloses a method for preparing sucralose-6-acetate in a biphasic liquid-liquid system. The method comprises slowly dropwise adding an inert non-polar solvent containing a chlorinating agent to an N,N-dimethyl formamide (DMF) solution of sucrose-6-acetate; then reacting the biphasic liquid-liquid mixture at a certain temperature for 9-20 hours; cooling the system to room temperature after stopping heating, and settling the solution to form layers, an upper layer being an inert non-polar solvent layer, and a lower layer being a DMF solution layer containing the product; hydrolyzing, neutralizing, and filtering the lower layer to obtain a filtrate, and then concentrating the filtrate to obtain a concentrate; dissolving the concentrate in water, and obtaining the product by extraction using ethyl acetate and crystallization, the inert non-polar solvent being an alkane solvent containing 8-18 carbon atoms that is not mutually soluble with DMF. The method has a high product yield, and can significantly reduce the decomposition of DMF, thereby reducing costs.

9 Claims, No Drawings

METHOD FOR PREPARING SUCRALOSE-6-ACETATE IN BIPHASIC LIQUID-LIQUID SYSTEM

This is a U.S. national stage application of PCT Application No. PCT/CN2017/084877 under 35 U.S.C. 371, filed May 18, 2017 in Chinese, claiming priority of Chinese Application No. 201611038346.6, filed Nov. 11, 2016, all of which are hereby incorporated by reference.

FIELD OF THE INVENTION

The present invention relates to the field of chemical production techniques. In particular, the present invention relates to a method for preparation of sucralose-6-acetate in a biphasic liquid-liquid system.

BACKGROUND ART

Sucralose is the sole new functional sweetener made from sucrose, featuring in zero energy, high and pure sweetness as well as high level of safety. Sucralose is one of the optimal sweeteners at present, and widely used in beverage, food, medicine and cosmetics industries.

Sucralose-6-acetate is a critical intermediate for synthesis of sucralose. Presently almost all synthesis routes for preparation of sucralose-6-acetate involve chlorination between sucrose-6-acetate and the Vilsmeier reagent. Chlorination is a critical reaction for synthesis of sucralose. The Vilsmeier reagent used for chlorination is mainly prepared through reaction between tertiary amine (such as N,N-dimethylformamide, namely DMF) and chlorinating agent (such as thionyl chloride, phosphorus oxychloride, phosgene, triphosgene, oxalyl chloride and so on).

The reaction between Vilsmeier reagent and sucrose-6-acetate was firstly reported by Mufi (U.S. Pat. No. 4,380,476). Later, there were various patent reports on improvement to this route both in China and abroad and the reported methods basically relates to homogenous solvent reaction system. For instance:

In the patent CN 101619083, Yancheng Jiekang Inc Disclosed a method for preparation of sucralose-6-acetate wherein, in solvents such as aromatic hydrocarbon, alicyclic hydrocarbon and halohydrocarbon, thionyl chloride is used in an in-situ reaction with DMF of molar equivalents to make a Vilsmeier reagent, then react with sucrose-6-acetate to make sucralose-6-acetate. However, the solvents used for the reaction are poor solvents of sulfur dioxide. Obviously, a large amount of sulfur dioxide gas produced simultaneously with reaction is unfavorable for environmental protection.

In the granted patent CN 101270136, Niutang Chemical Plant Co Ltd disclosed a method for preparation of sucralose-6-acetate by preparing a Vilsmeier reagent through an in-situ reaction between chlorinating agents such as, thionyl chloride and phosgene, and DMF, then reacting the Vilsmeier reagent with sucrose-6-acetate in a DMF solvent. The chlorination process is mainly characterized in that the temperature is to be increased to 90-98° C., and preserved for 6-15 hours. Because the large amount of chlorine hydride produced during reaction may result in decomposition of DMF, this method may increase production cost of sucralose.

Actually, because DMF is sensitive to acids, and high temperature is required to improve the yield of sucralose, it is inevitable that a large amount of chlorine hydride produced during the reaction process will result in the decomposition of DMF. Furthermore, as a result of preparation of sucralose per mole, 2-20 mole of DMF is decomposed into dimethylamine (U.S. Pat. No. 8,912,320).

However, there are very few technical solutions on reduction of decomposition of DMF during chlorination of sucrose-6-acetate at present.

Niutang Chemical Plant Co Ltd. disclosed a method for preparation of sucralose-6-acetate in the granted patent CN102070678, in which the solvent for reaction is chlorinated ether. This method emphasized that chlorine hydride or sulfur dioxide generated by the reaction system will soon depart from the reaction system, which can effectively improve reaction yield, and minimize consumption of DMF. However, (1) a large amount of sulfur dioxide produced during reaction is unfavorable for environmental protection; (2) as compared with DMF, chlorinated ether has higher toxicity, and is more expensive; (3) as sucrose-6-acetate has poor solubility in the chlorinated ether, chlorinated ether used as the solvent may result in instable reaction, poor reproduction and even carbonization.

In WO2015/092374, Tate & Lyle Public Limited Company disclosed a method for preparation of sucralose-6-acetate by using expensive perfluorooctane as a synergetic solvent; wherein, perfluorooctane can only improve reaction yield (increased by 3% approximately);. However, it is essential to add certain amount of sulfolane if it is necessary to minimize decomposition of DMF at the same time; there will undoubtedly make the solvent system and recycling of solvent more complicated.

In conclusion, an environment friendly method for preparing sucralose-6-acetate that can minimize decomposition of DMF, and improve yield is favorable for reduction of production cost for sucralose.

SUMMARY OF THE INVENTION

The problem to be solved by the present invention:

The present invention aims to solve the problem with excessive decomposition of MDF by chlorine hydride during preparation of sucralose-6-acetate with existing technologies, and provide an environment friendly high-yield method for preparing sucralose-6-acetate that can significantly reduce decomposition of DMF and cost.

Solution for settlement of the problem:

The technical solution provided by the present invention is a method for preparing sucralose-6-acetate in a biphasic liquid-liquid system, comprising the following steps:

1) In a biphasic liquid-liquid system formed by an inert non-polar solvent and N,N-dimethylformamide (abbreviated as DMF), sucrose-6-acetate and chlorinating agent engaging in chlorination reaction through heating; proceeding with cooling, settling the solution to form layers upon completion of the reaction, and then obtaining DMF solution layer containing the product;

2) Proceeding with hydrolyzed neutralization of the DMF solution layer containing the product as obtained in Step 1) to further obtain the filtrate through filtration;

3) Proceeding with concentration, extraction and crystallization of the filtrate obtained in Step 2) to further obtain the product—sucralose-6-acetate;

The inert non-polar solvent as described in Step 1) is an alkane solvent containing 8-18 carbon atoms, which is not mutually soluble with DMF.

During experiments, inventors were surprised to find that using a biphasic liquid-liquid system as formed by alkane of high boiling point and DMF for chlorination of sucrose-6-acetate can significantly reduce the decomposition of DMF during a heating process, which can obtain sucralose-6-acetate at a high yield at the same time. According to our analysis, the reason why alkane of a high boiling point can significantly reduce the decomposition of DMF is attributed to increasing solubility of alkane of a high boiling point and DMF at a high temperature as well as a solvation between long chain of alkane of high boiling point and DMF that can weaken the interaction between HCl and DMF. As discovered through the study, alkane of a high boiling point is available for better settling the solution to form layers with DMF at room temperature, which is favorable for recycle of alkane of a high boiling point.

The chlorinating agent is phosgene or solid phosgene.

The biphasic liquid-liquid system is clear biphasic system formed by DMF and alkane with 8-18 carbon atoms that is insoluble with DMF.

The inert non-polar solvent can be paraffin solvent, in particular, comprises one or more solvents selected from the group consisting of octane, nonane, decane, undecane, dodecane, isooctane, and isodecane.

Typically, the consumption of the phosgene is 7-11 molar equivalents of sucrose-6-acetate; consumption of solid phosgene used is 2.33-3.67 molar equivalents of sucrose-6-acetate; consumption of the inert non-polar solvent is equivalent to 2-10 times of mass of sucrose-6-acetate; consumption of the DMF is equivalent to 2-30 times of the mass of sucrose-6-acetate.

The following feeding mode according to the present invention is as follows: dissolving phosgene or solid phosgene in the inert non-polar solvent, and slowly dropping into the N,N-dimethylformamide (DMF) solution of sucrose-6-acetate at the temperature of 0-20° C.; after that, agitating the reaction mixture at room temperature until the system becomes transparent biphasic liquid-liquid mixture.

The heating condition is stated as follows: heating the biphasic liquid-liquid mixture at 90-100° C. for 9-20 hours;

Cooling down the biphasic liquid-liquid system to room temperature after completion of the reaction, settling the solution to form layers, wherein the upper layer is the inert non-polar solvent layer; the bottom layer is the DMF solution layer containing the product; wherein, inert non-polar solvent on the upper layer is available for direct circulation and use; proceeding with hydrolyzed neutralization of bottom layer to obtain the filtrate through filtration, and further obtaining the concentrate through concentration; adding water to dissolve the concentrate to obtain the product through extraction with acetic ether and crystallization.

Beneficial effect of the present invention:

(1) Preparation of sucralose-6-acetate in the biphasic liquid-liquid system features in high reaction yield, which can effectively minimize decomposition of DMF;

(2) It is applicable to obtain the upper-layer non-polar solvent through simple layering in the biphasic liquid-liquid system, which requires no rectification;

(3) The upper-layer non-polar solvent in the biphasic liquid-liquid system is available for direct circulation and use.

The present invention is described in detail as follows in combination with non-restrictive Examples.

DETAILED DESCRIPTION OF THE INVENTION

The present invention is further described in detail with reference to the following non-limiting embodiments.

EXAMPLE 1

Comparative Example: Using DMF as the Only Reaction Solvent

Solid phosgene (6.8 kg) was added into the N,N-dimethylformamide (DMF, 24.8 kg) solution of sucrose-6-acetate in batches at the temperature of 0-5° C. The reaction mixture was agitated at room temperature upon completion of addition until the system becomes transparent homogenous solution. After that, the system was heated at the temperature of 96° C. for reaction for 13 hours. The reaction was stopped, and the system was cooled down to room temperature. Hydrolyzed neutralization was conducted to obtain the filtrate through filtration. The filtrate was concentrated to obtain the concentrate. Water was added to dissolve the concentrate to obtain 2.22 kg product with yield up to 67% through extraction with acetic ether and crystallization.

According to the test of high performance liquid chromatography, 2.2 kg DMF was consumed by per kilogram sucrose-6-acetate.

EXAMPLE 2

Comparative Example: Using Toluene-DMF System as Reaction Solvent 6.8 kg of phosgene was added into 16 kg of toluene to obtain a toluene solution of phosgene. The solution was slowly added into N,N-dimethylformamide (DMF, 32 kg) solution of sucrose-6-acetate (2.9 kg) at the temperature of 10-15° C. The reaction mixture was agitated at room temperature upon completion of addition until the system becomes transparent homogenous solution. After that, the system was heated at the temperature of 96° C. for reaction for 13 hours. The reaction was stopped, and the system was cooled down to room temperature. Hydrolyzed neutralization was conducted to obtain the filtrate through filtration. The filtrate was concentrated to obtain the concentrate. Water was added to dissolve the concentrate to obtain 2.09 kg product with yield up to 63% through extraction with acetic ether and crystallization.

As shown by the high performance liquid chromatography test, every 2.25 kg of DMF was consumed by every 1 kg of sucrose-6-acetate.

EXAMPLE 3

A Biphasic Liquid-Liquid Solvent System 6.8 kg of phosgene was dissolved in 11.3 kg of octane to obtain the octane solution. The solution was slowly added into N,N-dimethylformamide (DMF, 24.9 kg) solution of sucrose-6-acetate (2.9 kg) at the temperature of 10-15° C. The reaction mixture was agitated at room temperature upon completion of addition until the system becomes transparent biphasic liquid-liquid mixture. After that, the system was heated at the temperature of 96° C. for reaction for 13 hours. The reaction was stopped, and the biphasic liquid-liquid system was cooled down to room temperature and allowed to stand to form layers. The upper layer is the inert non-polar solvent layer. The bottom layer is a DMF solution layer containing the product. Hydrolyzed neutralization was conducted to obtain the filtrate through filtration. The filtrate was concentrated to obtain the concentrate. Water was added to dissolve the concentrate to obtain 2.36 kg of the product with a yield up to 71% and HPLC purity over 99% through extraction with acetic ether and crystallization.

As shown by the high performance liquid chromatography test, every 1.21 kg of was consumed by every 1 kg of sucrose-6-acetate.

As compared with Example 1, product yield was improved by 4%, and consumption of DMF by sucrose-6-acetate per kilogram was reduced by 0.99 kg.

EXAMPLE 4

Biphasic Liquid-Liquid Solvent System 6.8 kg of phosgene was dissolved in 17 kg of dodecane to obtain a dodecane solution of the phosgene. The solution was slowly added into N,N-dimethylformamide (DMF, 32.3 kg) solution of sucrose-6-acetate (2.9 kg) at the temperature of 10-15° C. The reaction mixture was agitated at room temperature upon completion of addition until the system becomes transparent biphasic liquid-liquid mixture. After that, the system was heated at the temperature of 100° C. for reaction for 11 hours. The reaction was stopped, and the biphasic liquid-liquid system was cooled down to room temperature and allowed to stand to form layers. The upper layer is the inert non-polar solvent layer. The bottom layer is a DMF solution layer containing the product. Hydrolyzed neutralization was conducted to obtain the filtrate through filtration. The filtrate was concentrated to obtain the concentrate. Water was added to dissolve the concentrate to obtain 2.39 kg of the product with a yield up to 72% and HPLC purity over 99% through extraction with acetic ether and crystallization.

As shown by the high performance liquid chromatography tests, every 1.30 kg of DMF was consumed by every 1 kg of sucrose-6-acetate.

As compared with Example 1, the product yield was improved by 5%, and consumption of DMF by sucrose-6-acetate per kilogram was reduced by 0.90 kg.

EXAMPLE 5

Experiment on Recycle of Dodecane According to Example 4

6.8 kg of phosgene was dissolved in the dodecane obtained in Example 4 to further obtain dodecane solution of the phosgene. The solution was slowly added into a N,N-dimethylformamide (DMF, 32.3 kg) solution of sucrose-6-acetate (2.9 kg) at the temperature of 10-15° C. The reaction mixture was agitated at room temperature upon completion of addition until the system becomes transparent biphasic liquid-liquid mixture. After that, the system was heated at the temperature of 100° C. for reaction for 11 hours. The reaction was stopped, and the biphasic liquid-liquid system was cooled down to room temperature and allowed to stand to form layers. The upper layer is the inert non-polar solvent layer. The bottom layer is a DMF solution layer containing the product. Hydrolyzed neutralization was conducted to obtain the filtrate through filtration. The filtrate was concentrated to obtain the concentrate. Water was added to dissolve the concentrate to obtain 2.55 kg product with yield up to 77% and HPLC purity over 99% through extraction with acetic ether and crystallization.

As shown with high performance liquid chromatography, every 1.29 kg of DMF was consumed by every sucrose-6-acetate per kilogram.

As compared with Example 1, product yield can be improved by 10%, and consumption of DMF by sucrose-6-acetate per kilogram was reduced by 0.91 kg.

Embodiments of the Present Invention

Phosgene or solid phosgene was dissolved in the inert non-polar solvent, and slowly added into the N,N-dimethylformamide (DMF) solution of sucrose-6-acetate at the temperature of 0-20° C. After that, the reaction mixture was agitated at room temperature until the system became transparent biphasic liquid-liquid mixture. The biphasic liquid-liquid mixture was heated at the temperature of 90-100° C. for reaction for 9-20 hours. The biphasic liquid-liquid system was cooled to room temperature and allowed to stand to form layers. The upper layer was the inert non-polar solvent layer. The bottom layer was a DMF solution layer containing the product. Hydrolyzed neutralization of bottom layer was conducted to obtain the filtrate through filtration, and further obtain the concentrate through concentration. The DMF was recycled with conventional approaches in this field. Water was added to dissolve the concentrate to obtain the product through extraction with acetic ether and crystallization.

The inert non-polar solvent as described in the present invention was alkane solvent containing 8-18 carbon atoms, which was not insoluble with DMF. Such alkane can be linear, branched or cyclic one. In a preferred Example, it is linear or branched alkane. In a further preferred Example, it is octane, nonane, decane, undecane, dodecane, isooctane, isodecane or their mixture. The biphasic liquid-liquid system was a clear biphasic system formed by DMF and alkane containing 8-18 carbon atoms that is insoluble with the DMF.

Consumption of the phosgene as described in the present invention was equal to 7-11 molar equivalents of sucrose-6-acetate. Consumption of solid phosgene used was equal to 2.33-3.67 molar equivalents of sucrose-6-acetate. Consumption of the inert non-polar solvent was equivalent to 1.25-5 times of mass of phosgene or solid phosgene. Consumption of the DMF was equivalent to 1-3 times of the mass of inert non-polar solvent. The heating condition was stated as follows: the biphasic liquid-liquid mixture was heated at the temperature of 90-100° C. for reaction for 9-20 hours. The biphasic liquid-liquid system was subject to settle the solution to form layers upon completion of reaction, wherein the upper layer was an inert non-polar solvent layer, and the bottom layer was the DMF solvent layer containing the product. The inert non-polar solvent on the upper layer was available for direct circulation and use.

INDUSTRY APPLICABILITY (1) Preparation of sucralose-6-acetate in a biphasic liquid-liquid system, the reaction yield is high, and the decomposition of DMF can be effectively reduced;

(2) In the biphasic liquid-liquid system, the upper non-polar solvent is obtained by simple stratification operation, and does not need to be separated by rectification;

(3) The upper non-polar solvent in the biphasic liquid-liquid system can be directly circulated.

The invention claimed is:

1. A method for preparing sucralose-6-acetate in a biphasic liquid-liquid system, characterized in that method comprises the following steps:
   1) in the biphasic liquid-liquid system formed by an inert non-polar solvent and N,N-dimethylformamide, sucrose-6-acetate and a chlorinating agent engaging in chlorination through heating; cooling, settling the solution to form layers upon completion of reaction, and then taking a DMF (N,N-dimethylformamide) solution layer containing a product;

2) conducting hydrolysis and neutralization of the DMF solution layer containing the product as obtained in Step 1) to further obtain a filtrate through filtration;

3) proceeding with concentration, extraction and crystallization of the filtrate obtained in Step 2) to further obtain the product, which is sucralose-6-acetate;

wherein the inert non-polar solvent as described in Step 1) is an alkane solvent containing 8-18 carbon atoms, which is not mutually soluble with DMF;

wherein the alkane solvent as described in Step 1) is a paraffin solvent; and wherein the paraffin solvent is undecane or dodecane.

2. The method for preparing sucralose-6-acetate in a biphasic liquid-liquid system according to claim 1, characterized in that the chlorinating agent in Step 1) is phosgene or solid phosgene.

3. The method for preparing sucralose-6-acetate in a biphasic liquid-liquid system according to claim 1, wherein perfluorooctane is not used in the method; and wherein sulfolane is not used in the method.

4. The method for preparing sucralose-6-acetate in a biphasic liquid-liquid system according to claim 1, characterized in that the following feeding mode is adopted in Step 1): an inert non-polar solvent comprising the chlorinating agent is dropwise added into the N,N-dimethylformamide solution of sucrose-6-acetate, and stirred to form the biphasic liquid-liquid system.

5. The method for preparing sucralose-6-acetate in a biphasic liquid-liquid system according to claim 2, characterized in that the dosage of phosgene used as chlorinating agent is 7-11 molar equivalents of sucrose-6-acetate; whereas the dosage of solid phosgene used as chlorinating agent is 2.33-3.67 molar equivalents of sucrose-6-acetate.

6. The method for preparing sucralose-6-acetate in a biphasic liquid-liquid system according to claim 1, characterized in that mass of the inert non-polar solvent is 2-10 times of the mass of sucrose-6-acetate; whereas the mass of DMF is 2-30 times of the mass of sucrose-6-acetate.

7. The method for preparing sucralose-6-acetate in a biphasic liquid-liquid system according to claim 1, characterized in that the chlorination as described in Step 1) lasts for 9-20 hours at the temperature of 90-100° C.

8. The method for preparing sucralose-6-acetate in a biphasic liquid-liquid system according to claim 1, characterized in that the biphasic liquid-liquid system is subject to settle the solution to form layers upon completion of the chlorination; wherein, the upper layer is the inert non-polar solvent layer, and the bottom layer is the DMF solvent layer containing the product; the inert non-polar solvent on the upper layer is directly used for circulation.

9. A method for preparing sucralose-6-acetate in a biphasic liquid-liquid system, characterized in that method comprises the following steps:

1) in the biphasic liquid-liquid system formed by an inert non-polar solvent and N,N-dimethylformamide, sucrose-6-acetate and a chlorinating agent engaging in chlorination through heating; cooling, settling the solution to form layers upon completion of reaction, and then taking a DMF (N,N-dimethylformamide) solution layer containing a product;

2) conducting hydrolysis and neutralization of the DMF solution layer containing the product as obtained in Step 1) to further obtain a filtrate through filtration;

3) proceeding with concentration, extraction and crystallization of the filtrate obtained in Step 2) to further obtain the product, which is sucralose-6-acetate;

wherein the inert non-polar solvent as described in Step 1) is an alkane solvent containing 8-18 carbon atoms, which is not mutually soluble with DMF;

wherein the alkane solvent as described in Step 1) is a paraffin solvent;

wherein the inert non-polar solvent in Step 1) comprises one or more solvents selected from the group consisting of undecane and dodecane;

wherein the biphasic liquid-liquid system is subject to settle the solution to form layers upon completion of the chlorination;

wherein, the upper layer is the inert non-polar solvent layer, and the bottom layer is the DMF solvent layer containing the product; the inert non-polar solvent on the upper layer is directly used for circulation;

wherein the chlorinating agent in Step 1) is phosgene or solid phosgene;

wherein the following feeding mode is adopted in Step 1): an inert non-polar solvent comprising the chlorinating agent is dropwise added into the N,N-dimethylformamide solution of sucrose-6-acetate, and stirred to form the biphasic liquid-liquid system;

wherein the dosage of phosgene used as chlorinating agent is 7-11 molar equivalents of sucrose-6-acetate; whereas the dosage of solid phosgene used as chlorinating agent is 2.33-3.67 molar equivalents of sucrose-6-acetate;

wherein mass of the inert non-polar solvent is 2-10 times of the mass of sucrose-6-acetate; whereas the mass of DMF is 2-30 times of the mass of sucrose-6-acetate;

wherein the chlorination as described in Step 1) lasts for 9-20 hours at the temperature of 90-100° C.;

wherein perfluorooctane is not used in the method; and wherein sulfolane is not used in the method.

\* \* \* \* \*